(12) United States Patent
Kusu et al.

(10) Patent No.: US 12,207,914 B2
(45) Date of Patent: Jan. 28, 2025

(54) DIAGNOSTIC METHOD, DIAGNOSTIC SYSTEM, AND CONTROL METHOD OF DIAGNOSTIC SYSTEM

(71) Applicant: TERUMO KABUSHIKI KAISHA, Tokyo (JP)

(72) Inventors: Kohtaroh Kusu, Kanagawa (JP); Mitsuteru Yasunaga, Shizuoka (JP); Yusuke Sekine, Kanagawa (JP)

(73) Assignee: TERUMO KABUSHIKI KAISHA, Tokyo (JP)

( * ) Notice: Subject to any disclaimer, the term of this patent is extended or adjusted under 35 U.S.C. 154(b) by 808 days.

(21) Appl. No.: 16/953,464

(22) Filed: Nov. 20, 2020

(65) Prior Publication Data

US 2021/0068704 A1    Mar. 11, 2021

Related U.S. Application Data

(63) Continuation of application No. PCT/JP2019/022712, filed on Jun. 7, 2019.

(30) Foreign Application Priority Data

Jun. 11, 2018   (JP) .................................. 2018-111043

(51) Int. Cl.
   *A61B 5/06*    (2006.01)
   *A61B 5/00*    (2006.01)

(52) U.S. Cl.
   CPC ............ *A61B 5/061* (2013.01); *A61B 5/6852* (2013.01); *A61B 5/7405* (2013.01); *A61B 5/742* (2013.01); *A61B 5/746* (2013.01)

(58) Field of Classification Search
   CPC ..... A61B 5/061; A61B 5/6852; A61B 5/7405; A61B 5/742; A61B 5/746;

(Continued)

(56) References Cited

U.S. PATENT DOCUMENTS 5,158,084 A *  10/1992  Ghiatas ................... A61B 6/12
                                                              604/117
5,740,222 A    4/1998   Fujita et al.
(Continued)

FOREIGN PATENT DOCUMENTS

CN    102076378 A    5/2011
CN    108024693 A    5/2018
(Continued)

OTHER PUBLICATIONS

International Search Report (PCT/ISA/210) issued on Sep. 3, 2019, by the Japan Patent Office as the International Searching Authority for International Application No. PCT/JP2019/022712.

(Continued)

*Primary Examiner* — Patrick Fernandes
*Assistant Examiner* — Nicholas A Robinson
(74) *Attorney, Agent, or Firm* — Buchanan Ingersoll & Rooney PC

(57) ABSTRACT

A diagnostic method, a diagnostic system, and a control method of a diagnostic system that can detect specific behavior of an elongated body easily and with high accuracy are provided. The diagnostic method is a diagnostic method for diagnosing the behavior of a guiding catheter having a distal end and a proximal end in a biological lumen. The diagnostic method includes inserting the guiding catheter into the biological lumen from the distal end and detecting energy that has passed through a body after irradiating the inside of the body with the energy. The diagnostic method also includes identifying the position of the guiding catheter in the body by the detected energy and comparing the identified position of the guiding catheter with an expected position and detecting specific behavior of the guiding catheter from an amount of deviation of the position of the guiding catheter with respect to the expected position.

13 Claims, 7 Drawing Sheets

(58) Field of Classification Search
CPC ...... A61B 2017/3413; A61B 2090/376; A61B 2090/3966; A61B 90/37; A61B 6/032; A61B 6/4233; A61B 8/0841; A61B 2576/00; A61B 6/12
See application file for complete search history.

(56) References Cited

U.S. PATENT DOCUMENTS

| | | | | |
|---|---|---|---|---|
| 6,148,095 | A * | 11/2000 | Prause | A61B 6/504 600/467 |
| 6,618,612 | B1 | 9/2003 | Acker et al. | |
| 2004/0215070 | A1 * | 10/2004 | Letort | A61B 5/411 600/549 |
| 2005/0171426 | A1 | 8/2005 | Rasche | |
| 2007/0016070 | A1 | 1/2007 | Grunwald et al. | |
| 2008/0004431 | A1 * | 1/2008 | Kinnane | A61L 27/3604 530/356 |
| 2008/0161681 | A1 | 7/2008 | Hauck | |
| 2008/0275467 | A1 * | 11/2008 | Liao | A61B 6/032 703/11 |
| 2008/0294034 | A1 * | 11/2008 | Krueger | A61B 5/06 600/409 |
| 2009/0005675 | A1 | 1/2009 | Grunwald et al. | |
| 2010/0030250 | A1 * | 2/2010 | Warnack | A61M 25/10 606/194 |
| 2011/0160570 | A1 | 6/2011 | Kariv et al. | |
| 2011/0166410 | A1 | 7/2011 | Gutierrez et al. | |
| 2013/0046174 | A1 * | 2/2013 | Fischell | A61B 90/39 600/431 |
| 2014/0100450 | A1 | 4/2014 | Besz et al. | |
| 2015/0164607 | A1 * | 6/2015 | Ruijters | G06T 19/20 382/132 |
| 2015/0257849 | A1 * | 9/2015 | Barth | A61B 17/3403 600/424 |
| 2016/0135884 | A1 * | 5/2016 | Warner | A61B 5/333 600/509 |
| 2016/0287111 | A1 | 10/2016 | Jacobsen | |
| 2018/0256262 | A1 | 9/2018 | Duindam et al. | |
| 2019/0247017 | A1 * | 8/2019 | Minas | A61B 8/0891 |
| 2019/0255290 | A1 * | 8/2019 | Snyder | A61M 25/0053 |

FOREIGN PATENT DOCUMENTS

| | | |
|---|---|---|
| DE | 10 2014 204 702 A1 | 9/2015 |
| JP | 2005524435 A | 8/2005 |
| JP | 2008541799 A | 11/2008 |
| JP | 2010514515 A | 5/2010 |

OTHER PUBLICATIONS

Written Opinion (PCT/ISA/237) issued on Sep. 3, 2019, by the Japan Patent Office as the International Searching Authority for International Application No. PCT/JP2019/022712.
Office Action (The First Office Action) issued Mar. 10, 2022, by the National Intellectual Property Administration P.R. China in corresponding Chinese Patent Application No. 201980038908.2 and an English Translation of the Office Action. (14 pages).
The extended European Search Report issued Jul. 9, 2021, by the European Patent Office in corresponding European Patent Application No. 19819715.4-1126. (8 pages).

* cited by examiner

DIAGNOSTIC METHOD, DIAGNOSTIC SYSTEM, AND CONTROL METHOD OF DIAGNOSTIC SYSTEM

CROSS-REFERENCES TO RELATED APPLICATIONS

This application is a continuation of International Application No. PCT/JP2019/022712 filed on Jun. 7, 2019, which claims priority to Japanese Patent Application No. 2018-111043 filed on Jun. 11, 2018, the entire content of both of which is incorporated herein by reference.

FIELD OF THE INVENTION

The present disclosure generally relates to a diagnostic method, a diagnostic system, and a control method of a diagnostic system that are used for an intervention procedure.

BACKGROUND DISCUSSION

In recent years, as a treatment for an arterial lesion site in a lower limb, a procedure in which a catheter is introduced from an artery of an arm, for example, a radial artery, and a treatment is carried out (TRI: Trans Radial Intervention) has been carried out. Introducing a catheter from an artery of an arm can provide an effect that a relative physical burden on a patient can be reduced and, for example, the patient can be discharged from the hospital earlier.

When a catheter is introduced, general X-ray angiography is carried out in order to identify a position of the catheter and a position of a lesion site in the body. However, the patient is exposed to radiation when the X-ray angiography is carried out. Thus, it is preferable that a range in which the X-ray angiography is carried out is relatively small. Therefore, it can be difficult to observe the whole of the catheter inserted in a biological body by the X-ray angiography. However, the burden on the biological body may increase if the catheter exhibits unintentional behavior outside an X-ray contrast image.

For example, in U.S. Patent Application Publication No. 2011/0160570, a diagnostic method is described in which motion of a guide wire outside an X-ray contrast image is estimated when the guide wire moves in the X-ray contrast image.

In an elongated body that can be inserted in a biological body, such as a catheter, the length of the part disposed in the biological body is variable. For this reason, with only motion in an X-ray contrast image, it can be difficult to accurately grasp the behavior of the elongated body in some cases.

SUMMARY

A diagnostic method, a diagnostic system, and a control method of a diagnostic system are disclosed that can detect specific behavior of an elongated body rather easily and with relatively high accuracy.

In accordance with an aspect, a diagnostic method is disclosed for diagnosing behavior of an elongated body having a distal end and a proximal end in a biological lumen, and is characterized by having the following configuration. The diagnostic method includes inserting the elongated body into the biological lumen from the distal end and detecting energy that has passed through a body outside the body after irradiating the inside of the body with the energy from the outside of the body. The diagnostic method has also includes identifying the position of the elongated body in the body by the detected energy and comparing the identified position of the elongated body with an expected position that is the position of the elongated body in proper behavior and detecting specific behavior of the elongated body from the amount of deviation of the position of the elongated body with respect to the expected position.

In accordance with another aspect, a diagnostic system is disclosed that diagnoses behavior of an elongated body having a distal end and a proximal end in a body, and is characterized by having the following configuration. The diagnostic system includes an irradiating unit configured to irradiate the inside of the body with energy from the outside of the body, a detecting unit configured to detect the energy that has passed through the body outside the body, a control unit configured to identify the position of the elongated body in the body by the energy detected in the detecting unit, and a notifying unit configured to carry out notification allowed to be recognized by a visual sense or an auditory sense. The control unit is configured to read or calculate an expected position that is the position of the elongated body in proper behavior and calculates the amount of deviation of the identified position of the elongated body with respect to the expected position to cause the notifying unit to output a notification according to the calculated amount of deviation.

In accordance with a further aspect, a control method of a diagnostic system that diagnoses behavior of an elongated body having a distal end and a proximal end in a body, and is characterized by having the following configuration. The control method includes causing an irradiating unit to carry out irradiation with energy, causing a detecting unit to detect the energy, and receiving information on the detected energy from the detecting unit and identifying the position of the elongated body from the information. The control method also includes identifying an expected position that is the position of the elongated body in proper behavior, calculating the amount of deviation of the position of the elongated body with respect to the expected position, and causing a notifying unit that carries out notification allowed to be recognized by a visual sense or an auditory sense to notify a notification according to a calculated result.

The diagnostic method configured in the aforesaid manner can detect the specific behavior of the elongated body rather easily and with relatively high accuracy by detecting the amount of deviation of the elongated body with respect to the expected position.

In the diagnostic method, a tortuosity of the elongated body outside the irradiation range of the energy may be detected from the amount of deviation of the distal end of the elongated body toward the proximal side in the detecting of the specific behavior of the elongated body, which allows the present diagnostic method to detect a tortuosity of the elongated body outside the irradiation range of the energy rather easily and with relatively high accuracy even when the irradiation range of the energy is limited.

The diagnostic method may include detecting a proximal length that is a length in a longitudinal direction regarding the elongated body located outside the body, and the expected position may be identified based on the position of the distal end of the elongated body identified by the energy detected in the detecting unit and the proximal length. Due to this, even when the proximal length of the elongated body changes, the present diagnostic method can accurately identify the expected position that changes based on the variation amount of the proximal length. Therefore, the specific behavior of the elongated body can be detected rather easily and with relatively high accuracy by detecting the amount of deviation of the elongated body with respect to the expected position that changes.

In the diagnostic method, the elongated body may be inserted from a radial artery and be made to reach an artery of a lower limb in the inserting of the elongated body into the body, and a tortuosity of the elongated body in an ascending aorta may be detected in the detecting of the specific behavior of the elongated body. Due to this, while the elongated body located in the artery of the lower limb in which treatment is carried out is observed in the irradiation range of the energy, the occurrence of a tortuosity of the elongated body in the ascending aorta distant from the artery of the lower limb can be detected rather easily and with relatively high accuracy.

The expected position may be at least part of coordinate data of the biological lumen set in advance and that the elongated body is out of the biological lumen may be detected from the amount of deviation in the detecting of the specific behavior of the elongated body. Due to this, through detecting that the elongated body is out of the biological lumen, the occurrence of perforation or the like of the biological lumen by the elongated body can be detected rather easily and with relatively high accuracy.

The diagnostic method may include notifying a warning that can be recognized by the visual sense or the auditory sense when the amount of deviation is equal to or larger than a threshold set in advance or exceeds the threshold, which allows a physician to properly grasp the risk of the procedure, which can help improve the safety of the procedure.

The elongated body may be a guiding catheter in which another elongated body can be inserted. Due to this, the specific behavior of the guiding catheter can be detected rather easily and with relatively high accuracy by detecting the amount of deviation of the guiding catheter with respect to the expected position. Furthermore, in the guiding catheter, the proximal portion does not normally move relative to the biological body when another elongated body such as a treatment catheter or a guide wire made to pass through the inside is operated. In this case, because the expected position of the guiding catheter does not move, the detection of the amount of deviation of the guiding catheter with respect to the expected position is relatively easy. Therefore, by detecting the guiding catheter, a tortuosity of another elongated body operated inside the guiding catheter can be detected rather easily and with relatively high accuracy.

Furthermore, the diagnostic system configured in the aforesaid manner detects and notifies the amount of deviation of the elongated body with respect to the expected position and therefore can detect the specific behavior of the elongated body rather easily and with relative high accuracy.

The control unit of the diagnostic system may calculate the amount of deviation of the distal end of the elongated body toward the proximal side, which allows the diagnostic system to detect a tortuosity at any position between the distal end and the proximal end of the elongated body from the amount of deviation of the distal end of the elongated body toward the proximal side. Therefore, the diagnostic system can detect not only a tortuosity of the elongated body in the irradiation range of the energy but also a tortuosity of the elongated body outside the irradiation range.

The diagnostic system may have a proximal detecting unit configured to detect the elongated body located outside the body. In addition, the control unit may receive a detection result from the proximal detecting unit and calculate a proximal length that is a length in a longitudinal direction regarding the elongated body located outside the body and calculate the expected position based on the position of the distal end of the elongated body identified by the energy detected in the detecting unit and the proximal length. Due to this, even when the proximal length of the elongated body changes, the diagnostic system can accurately identify the expected position that changes based on the variation amount of the proximal length. Therefore, the diagnostic system can detect the amount of deviation of the elongated body with respect to the accurate expected position that moves and therefore can detect the specific behavior of the elongated body rather easily and with relatively high accuracy.

The control unit may employ at least part of coordinate data of a biological lumen set in advance as the expected position. Due to this, through detecting that the elongated body is out of the biological lumen, specific behavior such as perforation or the like of the biological lumen by the elongated body can be detected rather easily and with relatively high accuracy.

The control unit may cause the notifying unit to output a warning that can be recognized by the visual sense or the auditory sense when the amount of deviation is equal to or larger than a threshold set in advance or exceeds the threshold, which allows the physician to properly grasp the risk of the procedure from the notified warning, and which can help improve the safety of the procedure.

Moreover, the control method of a diagnostic system configured in the aforesaid manner causes the notifying unit to notify a notification according to the amount of deviation of the elongated body with respect to the expected position. Therefore, the physician that has received the notification can detect specific behavior of elongated body rather easily and with relatively high accuracy.

In accordance with an aspect, a diagnostic method is disclosed for diagnosing behavior of an elongated body having a distal end and a proximal end in a biological lumen, the diagnostic method comprising: inserting the elongated body into the biological lumen from the distal end; detecting energy having passed through a body after irradiating the body with the energy; identifying a position of the elongated body in the body by the detected energy; and comparing the identified position of the elongated body with an expected position and detecting specific behavior of the elongated body from an amount of deviation of the position of the elongated body with respect to the expected position.

In accordance with another aspect, a diagnostic system that diagnoses behavior of an elongated body having a distal end and a proximal end in a body, the diagnostic system comprising: an irradiating unit configured to irradiate an inside of the body with energy from outside of the body; a detecting unit configured to detect the energy that has passed through the body, and wherein the detecting unit is located outside of the body; a control unit configured to identify a position of the elongated body in the body by the energy detected in the detecting unit; a notifying unit configured to carry out notification by a visual sense or an auditory sense; and wherein the control unit is configured to read or calculate an expected position and calculate an amount of deviation of the identified position of the elongated body with respect to the expected position to cause the notifying unit to output a notification according to the calculated amount of deviation.

In accordance with a further aspect, a control method of a diagnostic system is disclosed that diagnoses behavior of an elongated body having a distal end and a proximal end in a body, the control method comprising: causing an irradiating unit to carry out irradiation with energy; causing a detecting unit to detect the energy; receiving information on the detected energy from the detecting unit and identifying a position of the elongated body from the information; identifying an expected position of the elongated body; calculating an amount of deviation of the position of the elongated body with respect to the expected position; and causing a notifying unit to carry out a notification by a visual sense or an auditory sense according to a calculated result from the amount of deviation of the position of the elongated body with respect to the expected position.

BRIEF DESCRIPTION OF THE DRAWINGS

FIGS. 5A and 5B illustrate a diagram depicting X-ray contrast images and wherein FIG. 5A depicts the state in which a distal tip of a guiding catheter falls within an irradiation range and FIG. 5B depicts the state in which the guiding catheter has been pulled back toward the proximal side due to a tortuosity.

FIGS. 6A and 6B illustrate a bar graph depicting the amount of deviation displayed on a display unit and wherein FIG. 6A depicts the state before the amount of deviation exceeds a threshold and FIG. 6B depicts the state in which the amount of deviation has exceeded the threshold.

FIGS. 10A and 10B illustrate a diagram depicting images obtained in the diagnostic system of FIG. 9 and wherein FIG. 10A depicts an image obtained by a first detecting unit and FIG. 10B depicts an image obtained by a second detecting unit.

DETAILED DESCRIPTION

Set forth below with reference to the accompanying drawings is a detailed description of embodiments of a diagnostic method, a diagnostic system, and a control method of a diagnostic system that are used for an intervention procedure representing examples of the inventive diagnostic method, diagnostic system, and control method disclosed here. Note that dimensions of the drawings are exaggerated and are different from actual dimensions in some cases for convenience of description. Furthermore, in the present disclosure and the drawings, regarding constituent elements having substantially the same functions, overlapping description is omitted by giving the same numeral thereto. In the present disclosure, the side inserted in a lumen will be referred to as "the distal side" and the hand side on which operation is carried out will be referred to as "the proximal side."

First Embodiment

Figure 1:
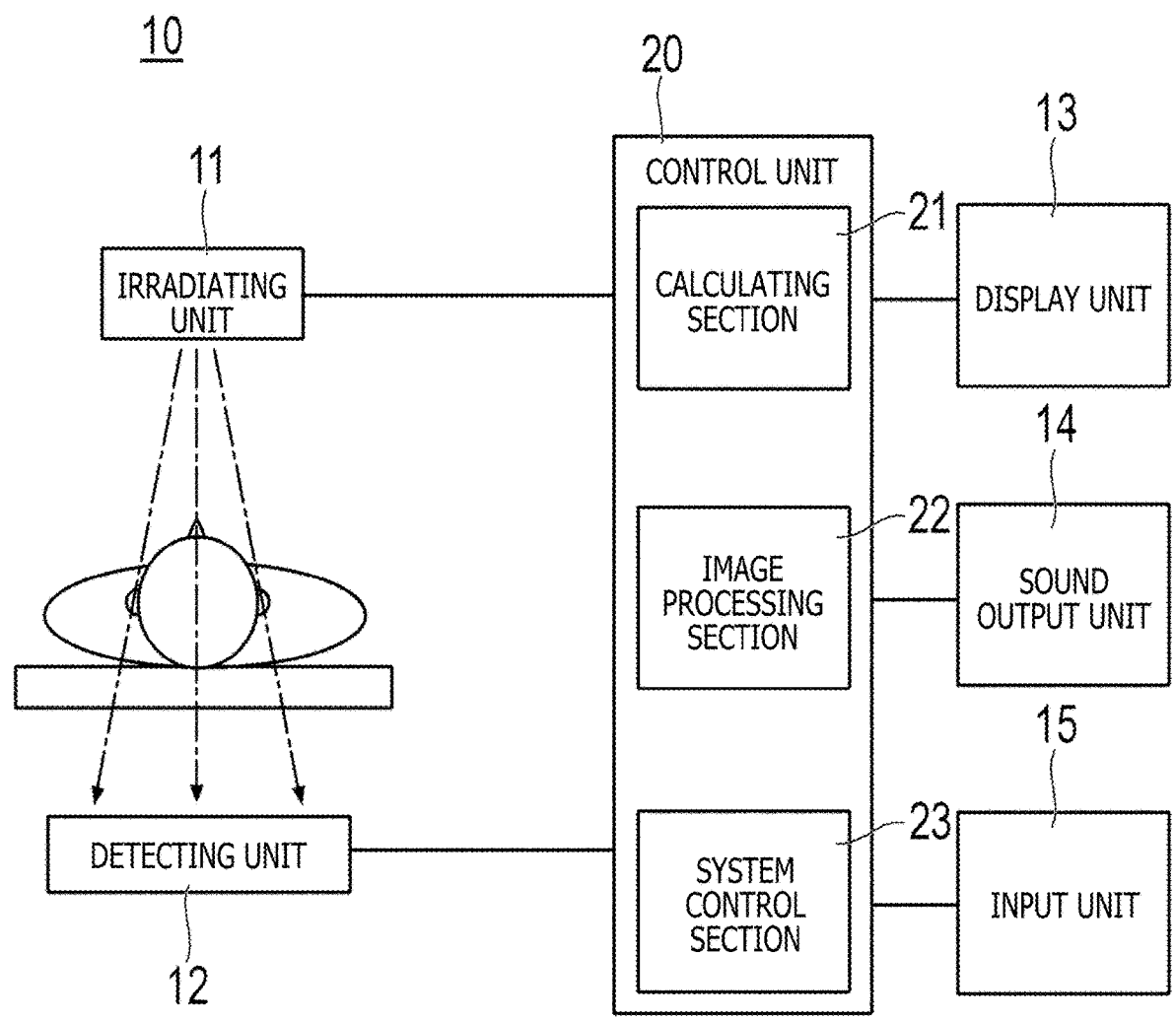
FIG. 1 is a configuration diagram depicting a diagnostic system according to a first embodiment.
Figure 2:
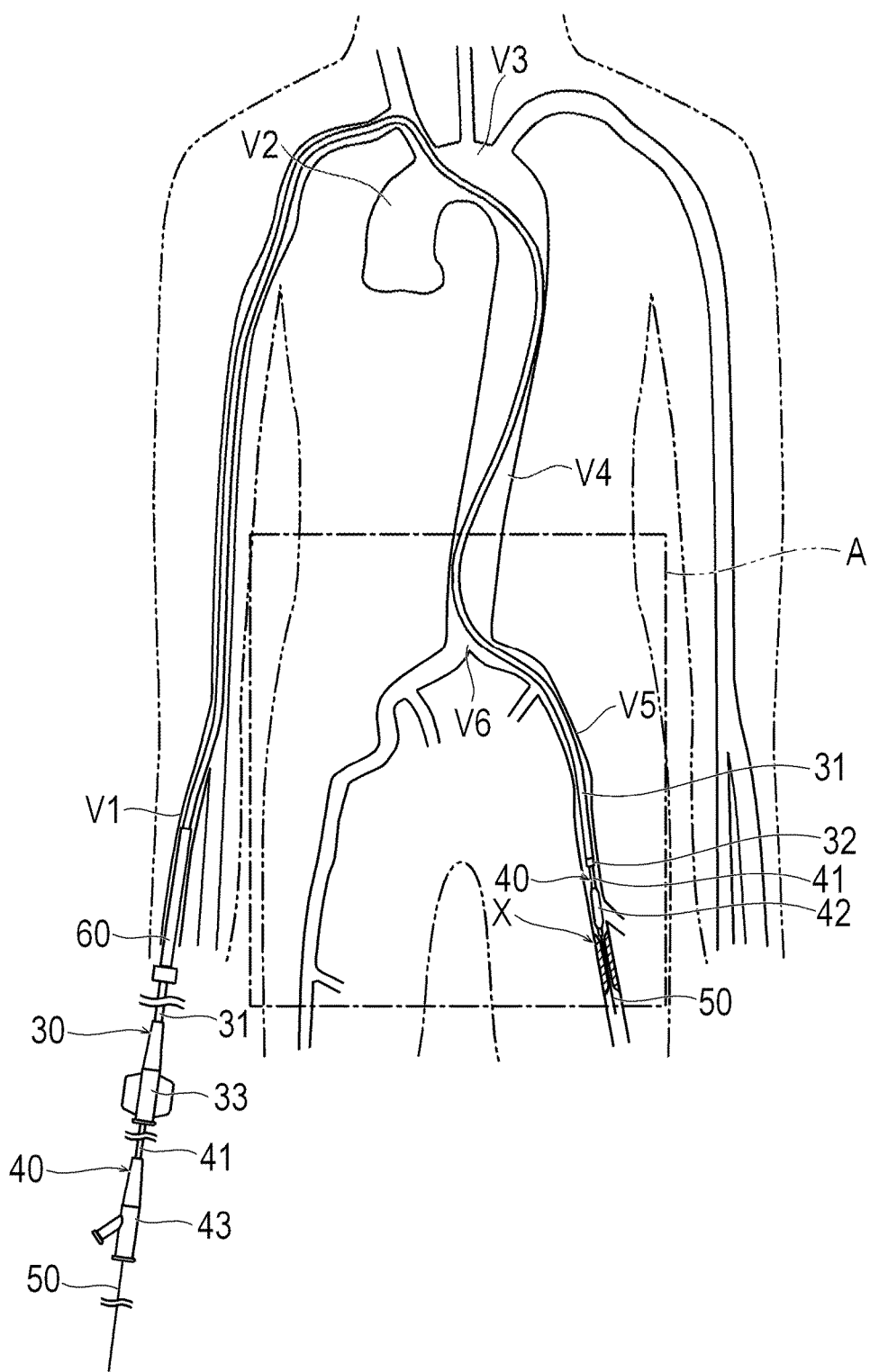
FIG. 2 is a plan view depicting the inside of blood vessels.
Figure 3:
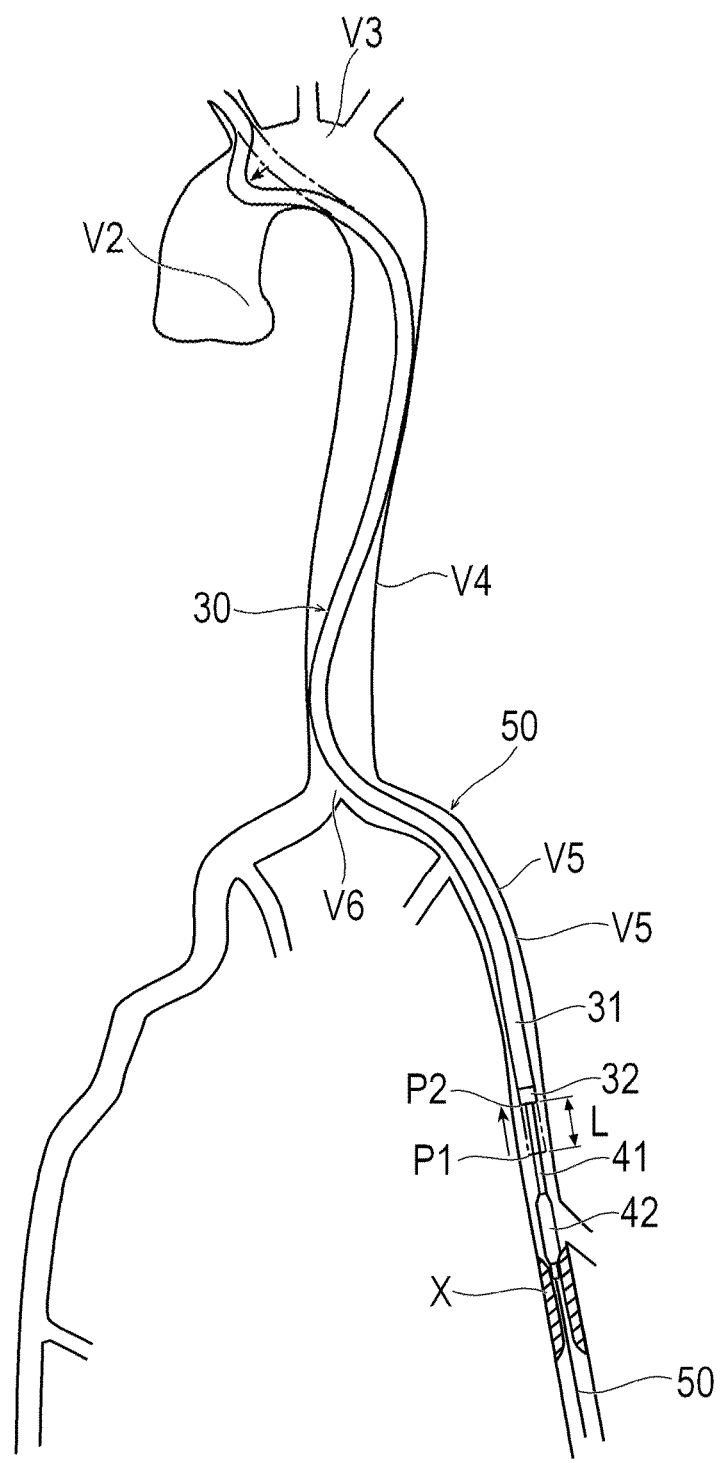
FIG. 3 is a plan view depicting part of the inside of blood vessels with magnification the inside of the blood vessels.

A diagnostic system 10 according to a first embodiment depicted in FIGS. 1 and 2 can be used to detect a tortuosity of a guiding catheter 30 and a treatment catheter 40 inserted in a blood vessel. The treatment catheter 40 treats a stenosis X of an artery V5 of the lower limb through a lumen of the guiding catheter 30 that has been introduced in a radial artery V1 of an arm of a patient and reached the artery V5 of the lower limb. The tortuosity means that, when the treatment catheter 40 and the guiding catheter 30 that are elongated are made to advance, the treatment catheter 40 and the guiding catheter 30 meander into a U-shape toward the upstream side of an ascending aorta V2 and the movement amount of the distal portion becomes smaller than the advancement amount of the proximal portion or the treatment catheter 40 and the guiding catheter 30 suddenly drop into the upstream side of the ascending aorta V2 and a catheter main body 31 kinks. The tortuosity rather easily occurs in a blood vessel having an inner diameter larger than the outer diameters of the treatment catheter 40 and the guiding catheter 30, for example, the ascending aorta V2 or the like. Therefore, when the treatment catheter 40 and the guiding catheter 30 are inserted from the radial artery V1 into an artery and are introduced into the ascending aorta V2, as depicted in FIG. 3, the treatment catheter 40 and the guiding catheter 30 rather easily get tortuous in such a manner as to drop in the direction in which the aortic valve is located (upstream direction of blood flow) in the region from the ascending aorta V2 to an aortic arch V3.

Note that the treatment to which the diagnostic system 10 is applied is not limited to the treatment of the artery V5 of the lower limb with introduction from the radial artery V1 of an arm since it may be difficult to accurately grasp the behavior of the elongated body inserted in a biological lumen with only motion in an X-ray contrast image, specifically, for example, it may be difficult to simultaneously observe tortuosities of the treatment site and the elongated body. For example, the case is disclosed in which the elongated body is introduced from the radial artery V1 and goes through the inside of the aorta to treat blood vessels of the head, for example, vertebral artery, carotid artery, arteries in the brain as peripheries of them, and so forth. Alternatively, the case is disclosed in which the elongated body is introduced from the radial artery V1 and goes through the inside of the aorta to treat blood vessels of the abdomen, celiac artery, renal artery, superior mesenteric artery, inferior mesenteric artery, and peripheral blood vessels of them, or the case of treating blood vessels of the head, for example, vertebral artery, carotid artery, and arteries in the brain as peripheries of them, from an artery of the lower limb, for example, common femoral artery. Alternatively, the case is disclosed in which the elongated body is introduced from the radial artery V1 or an artery of the lower limb to treat lumbar artery, splenic artery, left gastric artery, testicular artery, prostatic artery, uterine artery, artery of the lower limb, and so forth. As the treated arteries of the lower limb, aortoiliac bifurcation, common iliac artery, external iliac artery and internal iliac artery, common femoral artery, superficial femoral artery, deep femoral artery, popliteal artery (BTK), anterior tibial artery, peroneal artery, posterior tibial artery, dorsal artery of foot, plantar artery, and other peripheral arteries or collateral flow and so forth are disclosed.

First, the guiding catheter 30, the treatment catheter 40, and a guide wire 50 will be described.

As depicted in FIG. 2, the guiding catheter 30 includes the elongated catheter main body 31, a tubular distal tip 32 fixed to the distal portion of the catheter main body 31, and a hub 33 fixed to the proximal portion of the catheter main body 31. The distal tip 32 may be softer than the catheter main body 31 so that biological tissue may be kept from being damaged and the distal tip 32 includes X-ray contrast property. The distal tip 32 is formed through mixing of a material with relatively high X-ray contrast property into a soft resin material, for example. The material with relatively high X-ray contrast property (X-ray radiopacity), can be, for example, a metal such as platinum, gold, silver, iridium, titanium, or tungsten or an alloy of platinum, gold, silver, iridium, titanium, or tungsten. Furthermore, it is preferable that the catheter main body 31 also have X-ray radiopacity. However, the configuration of the catheter main body 31 is not limited to the catheter main body 31 as disclosed above.

The catheter main body 31 includes a lumen into which the treatment catheter 40 can be inserted from the hub 33. Thus, the guiding catheter 30 can guide the treatment catheter 40 to an intended position in a biological body.

The treatment catheter 40 can be a device that treats the stenosis X. The treatment catheter 40 can be a balloon catheter including a balloon 42 that can inflate, for example. The treatment catheter 40 includes a treatment catheter main body 41, the balloon 42 that is disposed at the distal portion of the treatment catheter main body 41 and can inflate, and a treatment hub 43 disposed at the proximal portion of the treatment catheter main body 41. Note that the treatment catheter 40 does not have to be a balloon catheter.

The guide wire 50 is inserted into the treatment catheter 40 and the guiding catheter 30, and the treatment catheter 40 and the guiding catheter 30 are made to advance to the intended position along the guide wire 50.

Next, the diagnostic system 10 will be described. As depicted in FIG. 1, the diagnostic system 10 includes an irradiating unit 11 that carries out irradiation with X-rays, a detecting unit 12 that detects the X-rays, a control unit 20 that identifies the occurrence of a tortuosity from the detected X-rays, a display unit 13 (notifying unit), a sound output unit 14 (notifying unit), and an input unit 15.

An X-ray angiography can generated by the irradiating unit 11 being supplied electrical power. As depicted in FIG. 2, the irradiating unit 11 irradiates a predetermined irradiation range A of the body of the patient with the X-rays. In accordance with an embodiment, it can be preferable that the irradiation range A be limited to only part of the body of the patient in order to set the exposure range of the patient as small as possible. The irradiation range A may be, for example, a range including the lower side of a descending aorta V4, an aortoiliac bifurcation V6, the upper side of the artery V5 of the lower limb, and the stenosis X.

As depicted in FIG. 1, the detecting unit 12 may be a planar FPD (Flat Panel Detector) or the like that receives X-rays and outputs an electrical signal. The detecting unit 12 is disposed at a position opposed to the irradiating unit 11 and a patient can be arranged between the irradiating unit 11 and the detecting unit 12.

The control unit 20 can include a calculating section 21, an image processing section 22, and a system control section 23 that comprehensively controls the whole of the system. The control unit 20 includes a storing circuit and an arithmetic circuit. The storing circuit stores a program and various parameters. The arithmetic circuit can be a CPU (Central Processing Unit), for example, and reads the program and various parameters from the storing circuit to execute arithmetic processing.

The image processing section 22 converts the electrical signal detected in the detecting unit 12 to image data that can be displayed on the display unit 13 as an image and causes the display unit 13 to display an X-ray image. Furthermore, the image processing section 22 can cause the display unit 13 to display a result calculated in the calculating section 21.

The calculating section 21 identifies the position of the distal end of the guiding catheter 30 from the electrical signal detected in the detecting unit 12. The calculating section 21 may identify the position of the distal end of the guiding catheter 30 from the image data resulting from processing in the image processing section 22. The calculating section 21 further calculates an amount D of deviation of the distal end of the guiding catheter 30. As depicted in FIG. 3, the amount D of deviation is an amount substantially proportional to a length L from an expected position P1 of the distal end of the guiding catheter 30 in the proper state in which an abnormality such as a tortuosity has not occurred to a position P2 of the distal end of the guiding catheter 30 in the state in which an abnormality such as a tortuosity has occurred.

The display unit 13 is a monitor that can display a visually-recognizable image. The displayed image may be a moving image, or alternatively, may be a still image. The display unit 13 displays an image based on an image signal received from the image processing section 22.

The sound output unit 14 may be a speaker or buzzer that outputs sound or voice that can be recognized by the auditory sense. The sound output unit 14 can notify a result calculated in the calculating section 21 by sound or voice.

The input unit 15 is used for the user to input data to the control unit 20. The input unit 15 can include a keyboard, a mouse, a microphone, a medium reading device, and so forth, for example.

Figure 4:
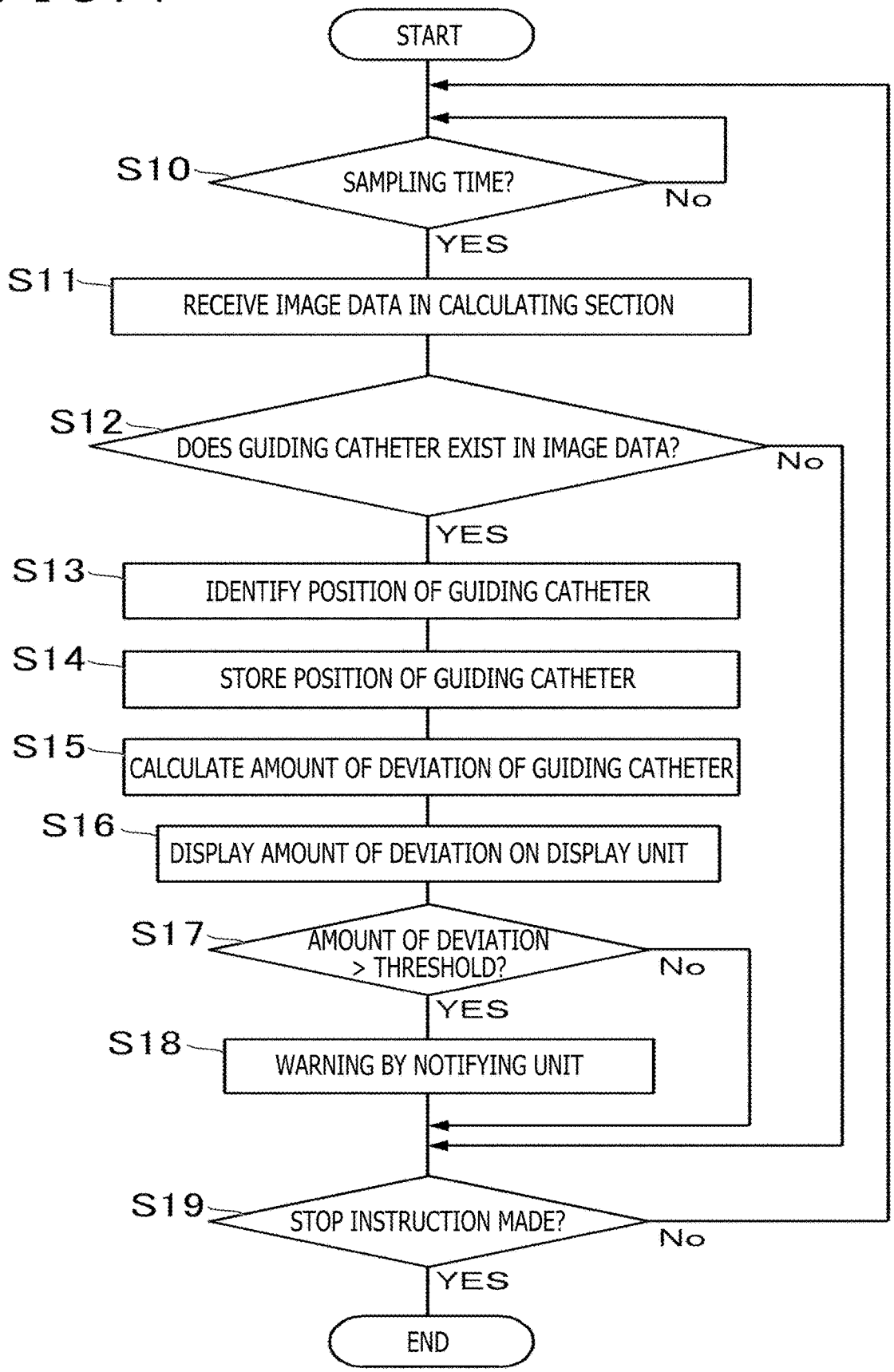
FIG. 4 is a flowchart depicting the flow of processing in a control unit.

Next, a diagnostic method using the diagnostic system 10 according to the first embodiment will be described with reference to a flowchart of the control unit 20 depicted in FIG. 4. Here, the description will be made by taking as an example the case of treating the stenosis X of the artery V5 of the lower limb of a patient as depicted in FIG. 2.

First, before the intervention procedure, the physician operates the input unit 15 depicted in FIG. 1 to start operation of the diagnostic system 10. When the operation of the diagnostic system 10 is started, the control unit 20 causes irradiation with X-rays from the irradiating unit 11 and causes the detecting unit 12 to detect X-rays that have passed through the body of the patient. The control unit 20 controls the image processing section 22 in such a manner that an electrical signal output based on a result detected in the detecting unit 12 is received in the image processing section 22. The image processing section 22 that has received the electrical signal creates two-dimensional image data that can be displayed on the display unit 13 for every sampling time when each image configuring a moving image is acquired. The image processing section 22 transmits the created image data to the display unit 13. When receiving the image data from the image processing section 22, the display unit 13 displays an image on a screen. In accordance with an embodiment, the created image may be a three-dimensional image.

Next, as depicted in FIG. 2, the physician carries out puncture on the right radial artery V1, for example, by a puncture needle and disposes a mini-guide wire in the blood vessel. Next, a sheath introducer 60 in which a dilator is inserted is introduced into the blood vessel along the mini-guide wire. Next, the dilator and the mini-guide wire are withdrawn. Subsequently, the guiding catheter 30 in which the guide wire 50 is inserted is introduced into the blood vessel through the sheath introducer 60. Alternatively, after the guide wire 50 is inserted into the sheath introducer and the sheath introducer is withdrawn, a guiding sheath with a lumen in which the dilator is inserted may be inserted along the guide wire 50.

Next, the guiding catheter 30 is pushed and advanced along the guide wire 50 to at least the inside of the aortic arch V3 of the patient. Specifically, the distal tip 32 of the guiding catheter 30 is advanced through the right radial artery, the right brachial artery, the right subclavian artery, and the brachiocephalic artery and reach the aortic arch V3. The distal tip 32 may further be advanced to go beyond the aortoiliac bifurcation V6 from the descending aorta V4 and be disposed in front of the stenosis X of the artery V5 of the lower limb. Next, the guide wire 50 is made to reach a position beyond the stenosis X. The physician can operate the guiding catheter 30 and the guide wire 50 while checking (i.e., observing) a moving image that falls within the irradiation range A and is displayed on the display unit 13.

Next, the proximal end of the guide wire 50 is inserted into a guide wire lumen of the treatment catheter 40 and the guide wire 50 is inserted into the guiding catheter 30. Next, the treatment catheter 40 is protruded from an opening part of the distal tip 32. The physician can carry out operation while making visual contact with the guiding catheter 30, the guide wire 50, and the treatment catheter 40 that fall within the irradiation range A and are displayed on the display unit 13.

Next, in the state in which the guiding catheter 30 is fixed at a position desirable for treatment by the treatment catheter 40, the physician operates the input unit 15 to start processing of detecting the occurrence of a tortuosity. When the processing of detecting the occurrence of a tortuosity is started, the control unit 20 determines whether or not the present time is the sampling time (step S10), and controls the calculating section 21 in such a manner that an electrical signal output in the detecting unit 12 based on a detection result is received in the calculating section 21 every sampling time (step S11).

Figure 5A:
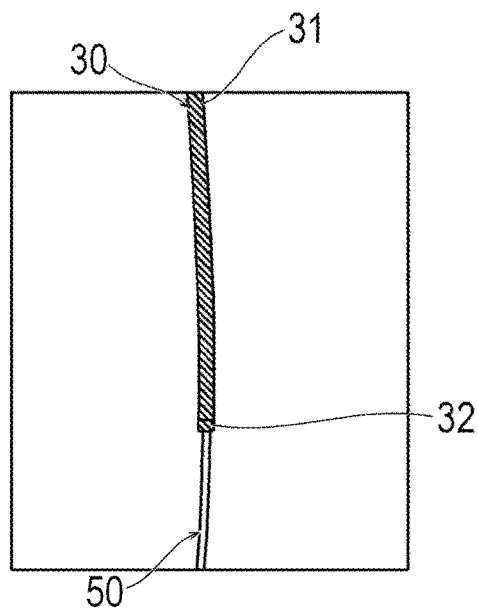
Figure 5B:
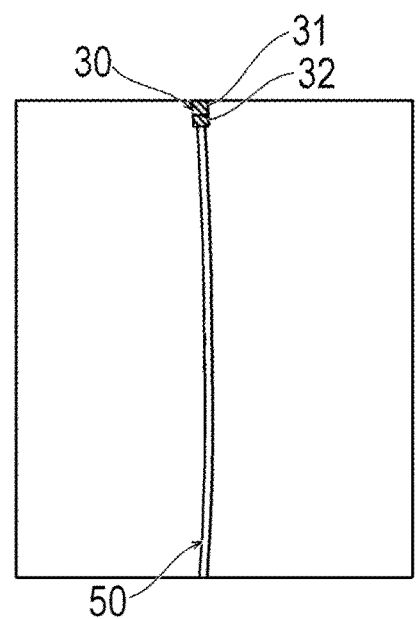

The calculating section 21 that has received the electrical signal creates image data as depicted in FIG. 5A and identifies the guiding catheter 30. Because the guiding catheter 30 has the distal tip 32 having X-ray contrast property, the calculating section 21 can determine the existence of the guiding catheter 30 by known image recognition techniques by comparing information on the distal tip 32 (for example, dimensions and shape) stored in the storing circuit of the control unit 20 in advance with the image data (step S12). When determining that the guiding catheter 30 exists in the irradiation range A, the calculating section 21 identifies the position of the guiding catheter 30 in the blood vessel (step S13). In the present embodiment, the position of the guiding catheter 30 is identified based on the position of the distal end of the guiding catheter 30. The position of the distal end of the guiding catheter 30 can be represented by various parameters. For example, as depicted in FIGS. 5A and 5B, the position of the distal end of the guiding catheter 30 can be represented by the area of occupation of the guiding catheter 30 (distal tip 32 and catheter main body 31) in the image data. That is, when the area of the guiding catheter 30 is larger in the image data, the distal end of the guiding catheter 30 reaches the distal side. Note that the catheter main body 31 located on the proximal side of the distal tip 32 has X-ray contrast property similarly to the distal tip 32 and therefore the catheter main body 31 can be identified from the X-ray image. The area of the guiding catheter 30 is substantially proportional to the length in the longitudinal direction regarding the guiding catheter 30 located in the irradiation range A and therefore is preferable as a parameter depicting the position of the distal end of the guiding catheter 30. Note that it is also possible for the calculating section 21 to identify the position of the distal end of the distal tip 32 based on coordinates from the image data. The calculating section 21 calculates the position of the distal end of the guiding catheter 30 every sampling time and causes the storing circuit to store the calculation result (step S14). Note that the calculating section 21 may calculate the position of the distal end of the guiding catheter 30 directly from the electrical signal of the detecting unit 12 without creating the image data from the electrical signal.

The calculating section 21 calculates the amount D of deviation by which the guiding catheter 30 has moved in the proximal direction from the expected position P1 of the guiding catheter 30 desirable for procedure of the treatment catheter 40 (step S15). The expected position P1 of the guiding catheter 30 is the position of the guiding catheter 30 when the physician has started the processing of detecting the occurrence of a tortuosity. Therefore, the physician can optionally set the expected position P1 of the distal end of the guiding catheter 30 by optionally starting the processing in the desirable state. Note that the expected position P1 of the distal end of the guiding catheter 30 may be automatically acquired as the position of the guiding catheter 30 in the state in which the guiding catheter 30 has been made to advance to the intended position after the processing by the calculating section 21 is started.

Figure 6A:
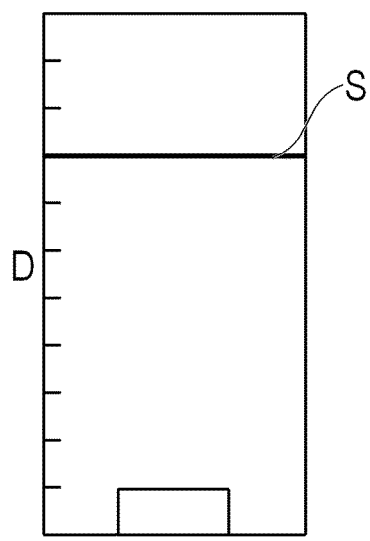

The calculated amount D of deviation is processed by the image processing section 22 and is transmitted to the display unit 13 together with X-ray image data to be displayed on the display unit 13 (step S16). For example, as depicted in FIG. 6A, the amount D of deviation of the distal end of the guiding catheter 30 in the proximal direction is displayed as a bar graph in which the length of a bar changes depending on the amount. In accordance with another embodiment, the amount D of deviation of the distal end of the guiding catheter 30 in the proximal direction may be displayed by another method. For example, the amount D of deviation may be displayed by a line graph, characters such as numerical values, colors that change depending on the value, and so forth.

Figure 6B:
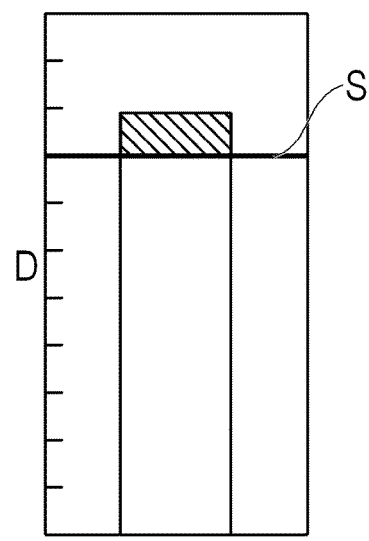

When the physician advances the treatment catheter 40 toward the distal side in the state in which the position of the introduction into the patient regarding the proximal portion of the guiding catheter 30 is fixed, the distal end of the treatment catheter 40 reaches the stenosis X as depicted in FIG. 2. When the treatment catheter 40 further advances toward the distal side so that the balloon 42 of the treatment catheter 40 may pass through the stenosis X, the balloon 42 receives resistance from the stenosis X. At this time, when the resistance which the balloon 42 receives from the stenosis X is high, the treatment catheter 40 bends and the movement length of the distal portion of the treatment catheter 40 becomes smaller than the advancement length of the proximal portion. Thus, the treatment catheter 40 may causes a tortuosity at any position in the longitudinal direction. When the treatment catheter 40 causes a tortuosity, the guiding catheter 30 in which the treatment catheter 40 is inserted also causes a tortuosity at the same position as the treatment catheter 40. When the treatment catheter 40 advances into the artery, the guiding catheter 30 is fixed at a position appropriate for use of the treatment catheter 40 differently from the treatment catheter 40. That is, the position of the proximal portion of the guiding catheter 30 does not move relative to the patient. For this reason, as depicted in FIGS. 3 and 5B, when a tortuosity occurs in the guiding catheter 30, the distal side of the guiding catheter 30 moves to return to the proximal side. Thus, by monitoring the distal end of the guiding catheter 30, a tortuosity that occurs not only in the irradiation range A but outside the irradiation range A can be detected. As depicted in FIGS. 6A and 6B, the physician can determine the tortuosity from the amount D of deviation of the guiding catheter 30 displayed on the display unit 13.

It is also possible for the calculating section 21 to cause the display unit 13 to display a warning according to the value of the amount D of deviation. The calculating section 21 reads out a threshold S stored in the storing circuit in advance and compares the threshold S with the calculated amount D of deviation (step S17). If the amount D of deviation exceeds the threshold S (or if the amount D of deviation is equal to or larger than the threshold S), the calculating section 21 causes the display unit 13 to display the warning (step S18). As the displayed warning, for example, the color of the part that exceeds the threshold S in the bar of the bar graph can be displayed as a different color as depicted in FIG. 6B, or characters depicting the warning can be displayed. Furthermore, it is also possible for the calculating section 21 to cause a sound or voice representing the warning to be output from, for example, the sound output unit 14 rather than the display unit 13. The threshold S is selected as appropriate and can be, for example, 20 mm to 150 mm, preferably 50 mm to 100 mm, in the present embodiment.

Figure 7:
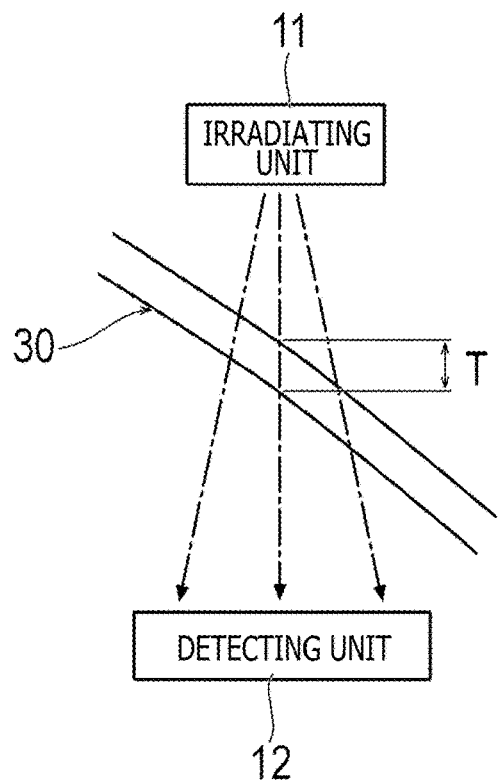
FIG. 7 is a diagram depicting the state in which the guiding catheter tilts in the irradiation direction of X-rays.

Furthermore, for example, when the guiding catheter 30 tilts in the irradiation direction of X-rays as depicted in FIG. 7, a thickness T along the irradiation direction of the guiding catheter 30 becomes larger and therefore the color depth of the two-dimensional image becomes larger in the two-dimensional image data. Therefore, the calculating section 21 can identify the tilt of the guiding catheter 30 with respect to the irradiation direction of X-rays by comparing the color density of the image data with a value set in advance. Accordingly, when the tilt of the guiding catheter 30 in the irradiation direction of X-rays is undesirable, the calculating section 21 can cause the display unit 13 and the sound output unit 14 to output a warning.

Moreover, coordinate data of the blood vessel travel of the patient may be acquired in advance by CT (Computed Tomography) or the like and at least part of the coordinate data of the blood vessel travel may be employed as the expected position P1. The deviation of the guiding catheter 30 can be detected by the amount D of deviation from the expected position P1 in the blood vessel from, which allows the physician to detect specific behavior such as perforation of the blood vessel by the guiding catheter 30 rather easily and with relatively high accuracy. The coordinate data of the blood vessel travel may be stored in the storing circuit of the control unit 20. However, the coordinate data may be stored in another device that can communicate with the control unit 20.

The physician can continue or review the procedure based on the notification of the amount D of deviation and the warning. For example, if the amount D of deviation exceeds the threshold S, the physician can move at least one of the guiding catheter 30 and the treatment catheter 40 to the proximal side and eliminate the tortuosity. After eliminating the tortuosity, the physician can operate the input unit 15 again and reset and resume the processing of detecting the occurrence of a tortuosity.

When the balloon 42 is inserted into the stenosis X, the physician attaches an inflator to the treatment hub 43 and injects a liquid. Thereby, the balloon 42 inflates and dilates the stenosis X. Next, the inflator is operated to drain the liquid and contract the balloon 42.

The physician can operate the input unit 15 at a timing desirable for the physician oneself and stop the processing of detecting the occurrence of a tortuosity (step S19). Due to this, the control unit 20 stops the processing by the calculating section 21. The physician moves the treatment catheter 40, the guide wire 50, and the guiding catheter 30 to the proximal side and withdraws the treatment catheter 40, the guide wire 50, and the guiding catheter 30 to outside of the body, which ends the treatment of the stenosis X.

As above, the diagnostic method of the first embodiment is a diagnostic method for diagnosing the behavior of the guiding catheter 30 having a distal end and a proximal end in a biological lumen. The diagnostic method includes inserting the guiding catheter 30 into the biological lumen from the distal end and detecting energy that has passed through a body outside the body after irradiating the inside of the body with the energy from the outside of the body. The diagnostic method also includes identifying the position of the guiding catheter 30 in the body by the detected energy and comparing the identified position of the guiding catheter 30 with an expected position P1 that is the position of the guiding catheter 30 in proper behavior and detecting specific behavior of the guiding catheter 30 from the amount D of deviation of the position of the guiding catheter 30 with respect to the expected position P1.

The diagnostic method configured in the aforesaid manner can detect the specific behavior of the guiding catheter 30 rather easily and with relatively high accuracy by detecting the amount D of deviation of the guiding catheter 30 with respect to the expected position P1.

In the diagnostic method, a tortuosity of the guiding catheter 30 outside the irradiation range A of the energy is detected from the amount D of deviation of the distal end of the guiding catheter 30 toward the proximal side in the detecting of the specific behavior of the guiding catheter 30, which allows the present diagnostic method to detect a tortuosity of the guiding catheter 30 outside the irradiation range of the energy rather easily and with relatively high accuracy even when the irradiation range A of the energy is limited.

In the diagnostic method, the guiding catheter 30 may be inserted from the radial artery V1 and be made to reach the artery V5 of the lower limb in the inserting of the guiding catheter 30 into the body, and a tortuosity of the guiding catheter 30 in the ascending aorta V2 may be detected in the detecting of the specific behavior of the guiding catheter 30. Due to this, while the guiding catheter 30 located in the artery V5 of the lower limb in which treatment is carried out is observed in the irradiation range A of the energy, the occurrence of a tortuosity of the guiding catheter 30 in the ascending aorta V2 distant from the artery V5 of the lower limb can be detected rather easily and with relatively high accuracy.

The expected position P1 may be at least part of coordinate data of the biological lumen set in advance and that the guiding catheter 30 is out of the biological lumen may be detected from the amount D of deviation in the detecting of the specific behavior of the guiding catheter 30. Due to this, through detecting that the guiding catheter 30 is out of the biological lumen, the occurrence of perforation or the like of the biological lumen by the guiding catheter 30 can be detected rather easily and with relatively high accuracy.

The diagnostic method includes notifying a warning that can be recognized by the visual sense or the auditory sense when the amount D of deviation is equal to or larger than the threshold S set in advance or exceeds the threshold S. The warning notification by the visual sense or the auditory sense can allow the physician the ability to properly grasp the risk of the procedure, which can improve the relative safety of the procedure.

The elongated body detected by the detecting unit 12 is the guiding catheter 30 in which another elongated body can be inserted. Due to this, the specific behavior of the guiding catheter 30 can be detected rather easily and with relatively high accuracy by detecting the amount D of deviation of the guiding catheter 30 with respect to the expected position P1. Furthermore, in the guiding catheter 30, the proximal portion does not normally move relative to the biological body when another elongated body such as the treatment catheter 40 or the guide wire 50 passes through the inside of the guiding catheter 30. In this case, because the expected position P1 of the guiding catheter 30 does not move, the detection of the amount D of deviation of the guiding catheter 30 with respect to the expected position P1 is rather easy. Therefore, by detecting the guiding catheter 30, a tortuosity of another elongated body operated inside the guiding catheter 30 can be detected rather easily and with relatively high accuracy.

Moreover, the diagnostic system 10 according to the first embodiment is the diagnostic system 10 that diagnoses the behavior of the guiding catheter 30 having a distal end and a proximal end in a living body. The diagnostic system 10 has the irradiating unit 11 that irradiates the inside of the body with energy from the outside of the body, the detecting unit 12 that detects the energy that has passed through the body outside the body, the control unit 20 that identifies the position of the guiding catheter 30 in the body by the energy detected in the detecting unit 12, and a notifying unit that carries out notification that can be recognized by the visual sense or the auditory sense of the physician. The control unit 20 reads or calculates the expected position P1, the expected position P1 being the position of the guiding catheter 30 in proper behavior (i.e., without tortuosity) and calculates the amount D of deviation of the identified position of the guiding catheter 30 with respect to the expected position P1 to cause the notifying unit to output a notification according to the calculated amount D of deviation.

The diagnostic system 10 configured in the aforesaid manner detects and notifies the amount D of deviation of the guiding catheter 30 with respect to the expected position P1 and therefore can detect the specific behavior of the guiding catheter 30 rather easily and with relatively high accuracy.

The control unit 20 calculates the amount D of deviation of the distal end of the guiding catheter 30 toward the proximal side, which allows the diagnostic system 10 to detect a tortuosity at any position between the distal end and the proximal end of the guiding catheter 30 from the amount D of deviation of the distal end of the guiding catheter 30 toward the proximal side. Therefore, the diagnostic system 10 can detect not only a tortuosity of the guiding catheter 30 in the irradiation range A of the energy but also a tortuosity of the guiding catheter 30 outside the irradiation range A.

The control unit 20 may employ at least part of coordinate data of a biological lumen as the expected position P1. Due to this, through detecting that the guiding catheter 30 is out of the biological lumen, specific behavior such as perforation or the like of the biological lumen by the guiding catheter 30 can be detected rather easily and with relatively high accuracy.

The control unit 20 causes the notifying unit to output a warning that can be recognized by the visual sense or the auditory sense when the amount D of deviation is equal to or larger than the threshold S set in advance or exceeds the threshold S, which allows the physician to properly grasp the risk of the procedure from the notified warning, which can help improve the safety of the procedure.

Furthermore, a control method of the diagnostic system 10 according to the first embodiment is a control method of the diagnostic system 10 that diagnoses the behavior of the guiding catheter 30 having a distal end and a proximal end in a body. The control method includes causing the irradiating unit 11 to carry out irradiation with energy, causing the detecting unit 12 to detect the energy, and receiving information on the detected energy from the detecting unit 12 and identifying the position of the guiding catheter 30 from the information. The control method can also include identifying the expected position P1 that is the position of the guiding catheter 30 in proper behavior, calculating the amount D of deviation of the position of the guiding catheter 30 with respect to the expected position P1, and causing a notifying unit that carries out notification that can be recognized by the visual sense or the auditory sense of the physician to notify a notification according to the calculated result.

The control method of the diagnostic system 10 configured in the aforesaid manner causes the notifying unit to notify the notification according to the amount D of deviation of the guiding catheter 30 with respect to the expected position P1. Therefore, the physician that has received the notification can detect specific behavior of the guiding catheter 30 rather easily and with relatively high accuracy.

Second Embodiment

Figure 8:
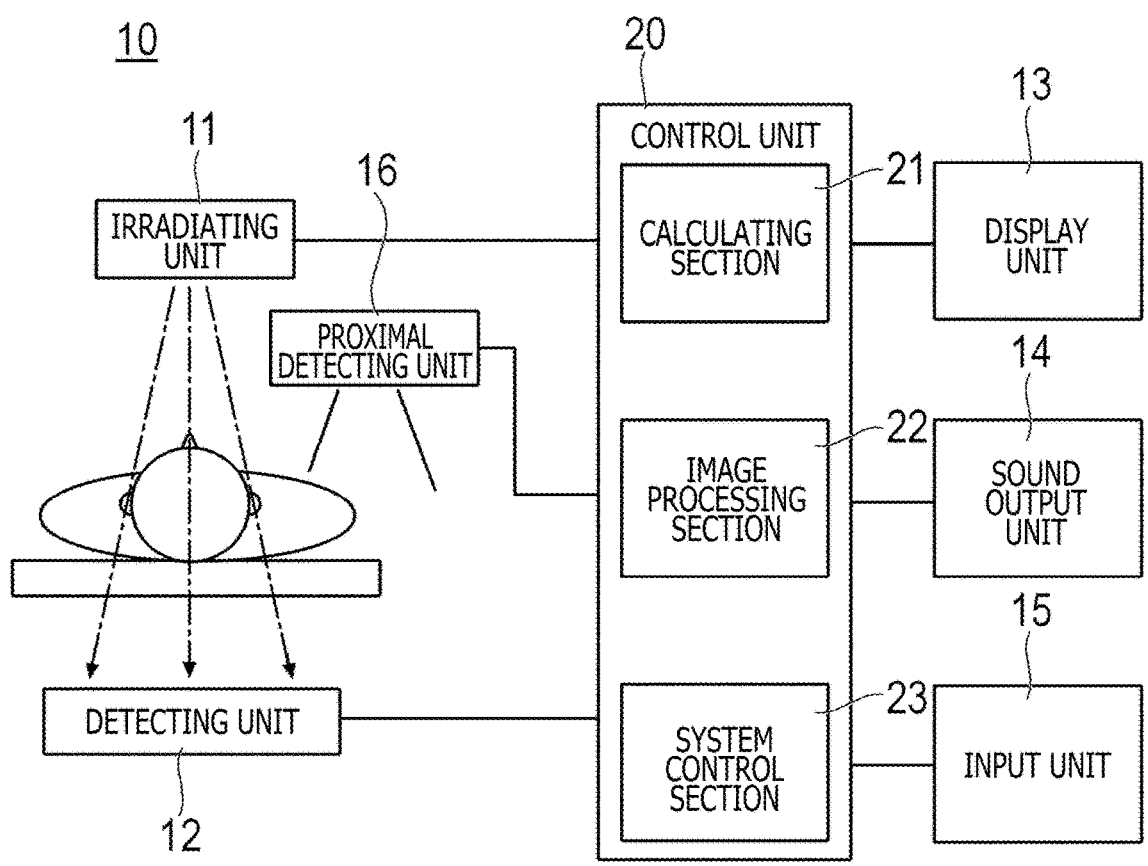
FIG. 8 is a configuration diagram depicting a diagnostic system according to a second embodiment.

The diagnostic system 10 according to a second embodiment is different from the first embodiment in that the diagnostic system 10 includes a proximal detecting unit 16 as depicted in FIG. 8.

In accordance with an embodiment, the proximal detecting unit 16 detects a position at which the guiding catheter 30 is inserted into the skin of the patient. The proximal detecting unit 16 can be a camera that can take a moving image, for example. Note that the proximal detecting unit 16 may image the proximal portion of the treatment catheter 40 or the proximal portion of the guide wire 50.

The calculating section 21 identifies a proximal length that is the length in the longitudinal direction regarding the guiding catheter 30 located outside the body of the patient from an electrical signal detected in the proximal detecting unit 16. The calculating section 21 identifies and stores the proximal length every sampling time and calculates the variation amount of the proximal length. Therefore, when the treatment catheter 40 is made to advance into an artery, the position of the proximal portion of the guiding catheter 30 may move relative to the patient. The calculating section 21 can relatively accurately calculate the expected position P1 at which the distal end of the guiding catheter 30 should exist according to the variation amount of the proximal length. The calculating section 21 may identify the proximal length by using a depth marker disposed on the surface of the catheter main body 31 of the guiding catheter 30. Furthermore, the proximal detecting unit 16 that detects the proximal length of the proximal portion of the guiding catheter 30 may be, for example, a sensor configured to capture motion attached to a hand of the physician or a sensor attached to the proximal portion of the guiding catheter 30 by coupling means such as a clip. The sensor attached to the proximal portion of the guiding catheter 30 can be a sensor that can be detected by another piece of detecting equipment. Moreover, the proximal detecting unit 16 that detects the proximal length of the guiding catheter 30 is disposed on an instrument around which the guiding catheter 30 is wound in order to hold the guiding catheter 30 and can detect the length by which the guiding catheter 30 is wound. The sensor can be, for example, a revolution indicator or the like.

As above, the diagnostic system 10 according to the second embodiment has the proximal detecting unit 16 that detects the guiding catheter 30 located outside the body of the patient. The control unit 20 receives the detection result from the proximal detecting unit 16 and calculates the proximal length that is the length in the longitudinal direction regarding the guiding catheter 30 located outside the body of the patient. In addition, the control unit 20 calculates the expected position P1 based on the position of the distal end of the guiding catheter 30 identified by energy detected in the detecting unit 12 and the proximal length. Due to this, even when the proximal length of the guiding catheter 30 changes, the accurate expected position P1 that moves can be set in consideration of the proximal length. Therefore, the amount D of deviation of the guiding catheter 30 with respect to the accurate expected position P1 that moves can be detected and thus specific behavior of the guiding catheter 30 can be detected rather easily and with relatively high accuracy.

Note that the method in which the detection result of the proximal detecting unit 16 is used for the calculation of the expected position P1 is particularly effective in the case of identifying a tortuosity of the treatment catheter 40 and the guide wire 50 whose proximal portions move.

The present disclosure is not limited to only the above-described embodiments and various changes can be made by those skilled in the art within the technical idea of the present disclosure. For example, the apparatus to acquire image data is not limited to the X-ray angiography and may be CT (Computed Tomography), MRI (Magnetic Resonance Imaging), ultrasound computed tomography, imaging using infrared rays, imaging using visible light, or the like. Furthermore, the image data to be acquired may be three-dimensional image data instead of two-dimensional image data.

Moreover, in the above-described embodiments, a tortuosity of the guiding catheter 30 is detected in order to identify a tortuosity of the treatment catheter 40. However, the configuration is not limited to the detecting of the guiding catheter 30 is detected in order to identify the tortuosity of the treatment catheter 40. For example, a tortuosity of the guiding catheter 30 may be detected in order to identify a tortuosity of the guide wire 50. Furthermore, a tortuosity of the treatment catheter 40 may be detected in order to identify a tortuosity of the guide wire 50. In addition, the elongated body about which a tortuosity is detected may be used alone and be detected instead of being used in combination with another elongated body.

Furthermore, continuation or review of the procedure based on the amount D of deviation and notification of a warning is not limited to determination by the physician and may be carried out by a third party or may be automatically carried out with reference to a past surgical operation record or big data. Alternatively, regularity or relevance may be found out from a large amount of data by using an artificial intelligence (hereinafter, AI) made to have learned past data and determination and prediction may be carried out. Moreover, with use of a multi-layered algorithm "deep neural network" modeled after the cranial nerve circuit of the human, correction and decision of setting of a threshold may be carried out by an AI.

Figure 9:
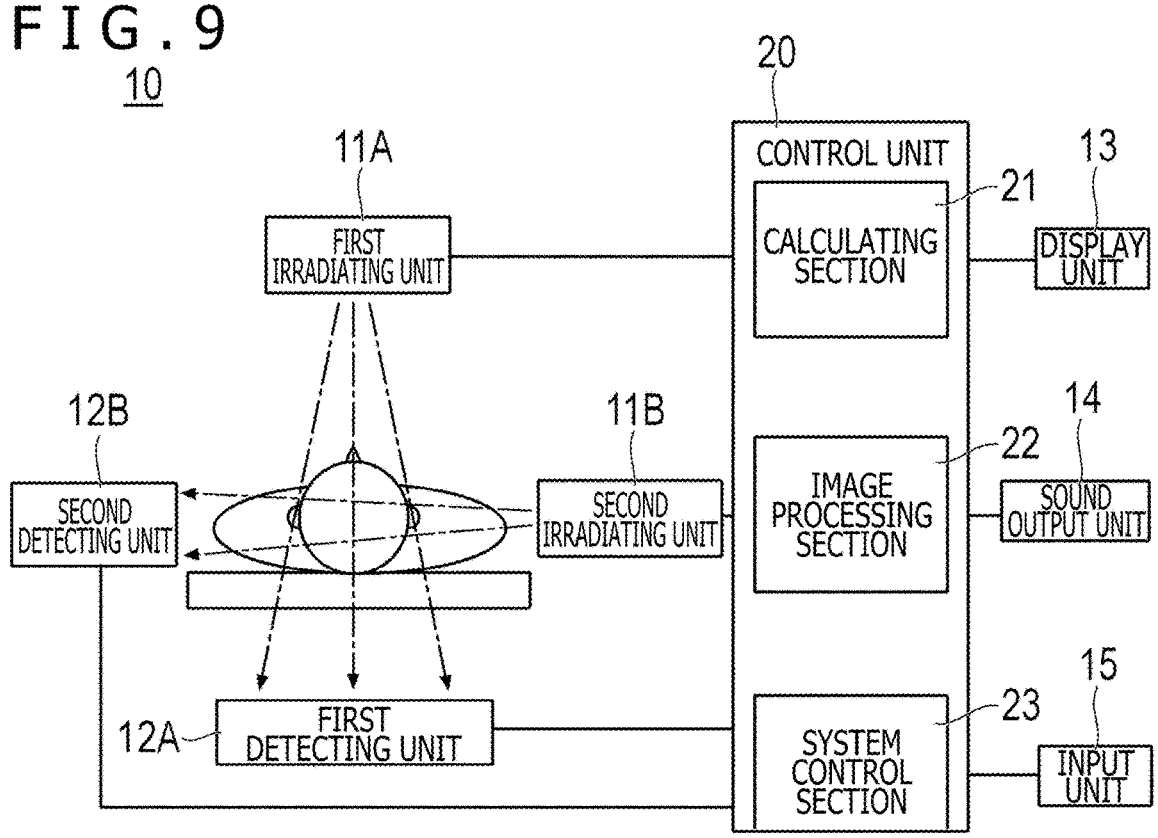
FIG. 9 is a configuration diagram depicting a modification example of the diagnostic system.
Figure 10A:
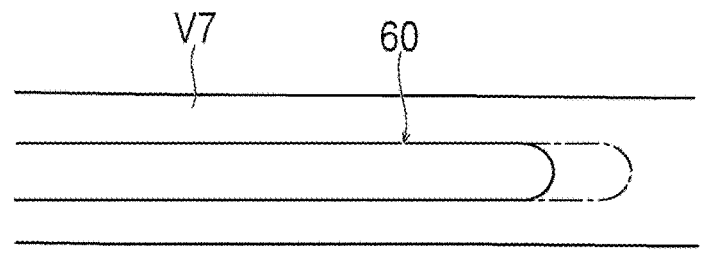
Figure 10B:
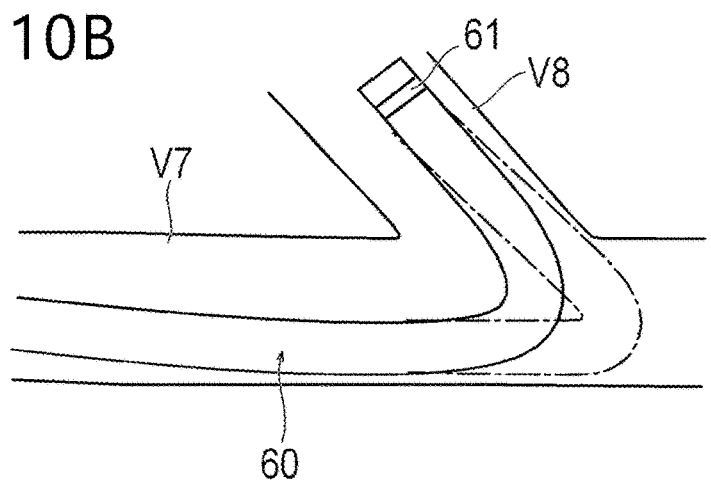

Furthermore, the image data may be acquired from not one direction but different two or more directions. For example, as in a modification example depicted in FIG. 9, the diagnostic system 10 includes a first irradiating unit 11A, a second irradiating unit 11B that carries out irradiation with energy from a different direction from the first irradiating unit 11A, a first detecting unit 12A that detects energy with which the irradiation is carried out from the first irradiating unit 11A, and a second detecting unit 12B that detects the energy with which the irradiation is carried out from the second irradiating unit 11B. For example, as depicted in FIGS. 10A and 10B, when a micro-catheter 60 (elongated body) is made to advance into a blood vessel V8 that branches at an acute angle from a main blood vessel V7, it is impossible to favorably detect the part that has entered the blood vessel V8 in the micro-catheter 60 from an image obtained by the first detecting unit 12A (see FIG. 10A) in some cases. However, there is a possibility that the part that has entered the blood vessel B8 in the micro-catheter 60 can be favorably detected from an image obtained by the second detecting unit 12B (see FIG. 10B). Therefore, movement of an X-ray marker 61 of the micro-catheter 60 can be detected by using the pieces of image data obtained from the different first detecting unit 12A and second detecting unit 12B, which make it possible to detect that the micro-catheter 60 overruns in the main blood vessel V7 as depicted by one-dot-chain lines in FIG. 10. In the first embodiment, the diagnostic system 10 may be used to prevent the guiding catheter 30 from advancing to the ascending aorta V2. In the present modification example, the diagnostic system 10 may be used to suppress excessive advancement of the micro-catheter 60 beyond necessity in the specific main blood vessel V7.

Moreover, the diagnostic system 10 may also be used for puncture under ultrasound guide. When puncture with a puncture needle is carried out from skin, an ultrasound tomographic image can be acquired by an ultrasound probe that outputs ultrasound and detects an ultrasound echo. The ultrasound probe can be a detecting unit as well as an irradiating unit. In the puncture needle, a cut surface is formed through oblique cutting in order to form a sharp needle tip. For this reason, in the puncture needle, a force of a vector toward the opposite direction to the cut surface acts on the needle tip at the time of puncture. Thus, the puncture needle gradually changes its direction and warps to deviate from the target. For this reason, due to the warpage of the puncture needle and penetration of the puncture needle to the outside of the target, the detection of the needle tip of the puncture needle by the ultrasound tomographic image becomes difficult in some cases. Even in such a case, by detecting the puncture needle by using the diagnostic system 10, specific behavior (for example, warpage) of the puncture needle can be rather easily detected through detection of the amount of deviation of the puncture needle. Note that the diagnostic system 10 may detect the movement speed of the puncture needle instead of detecting the amount of deviation of the puncture needle.

Furthermore, if machine learning is caused to determine the amount D of deviation and notification of a warning, signals obtained in the detecting unit 12, the first detecting unit 12A, the second detecting unit 12B, and the proximal detecting unit 16 do not need to be converted to images. Note that the machine learning may use image information similarly to the human and may use non-image information that cannot be determined by the human eye if the non-image information can be recognized and classified as a feature (for example, hardness of a lesion site).

Here, the image information refers to information that can be recognized and understood with the human eye and be used for diagnosis and refers to what is obtained by image conversion in electromagnetic wave information. Therefore, the non-image information refers to what is in such a state as to be impossible to recognize and understand as the shape of a blood vessel or a lesion site by the human eye and therefore be impossible to use for diagnosis, such as data such as digital bits described with "0" and "1" and quantum bits in which both states of "0" and "1" used in a quantum computer are superimposed on each other and DICOM information itself that is not displayed on a data structure or GUI. Alternatively, the non-image information may be information beyond the resolution of the human eye, such as what is relatively small and cannot be recognized by the human eye even when being enlarged because being beyond the resolution of the human eye, what cannot be separated into two points and is recognized as one point, and difference between light and shade in which difference in the grayscale cannot be recognized. The warning means that transmits deviation may be, in addition to displaying on a screen, sound, vibration (equivalent to vibration for notification by a smartphone put in a pocket), or a combination of two or more of them. The displaying, sound, and vibration may be set larger according to the amount D of deviation and the warning means may be increased like displaying on a screen and vibration.

The detailed description above describes embodiments of a diagnostic method, a diagnostic system, and a control method of a diagnostic system that are used for an intervention procedure. The invention is not limited, however, to the precise embodiments and variations described. Various changes, modifications and equivalents can be effected by one skilled in the art without departing from the spirit and scope of the invention as defined in the accompanying claims. It is expressly intended that all such changes, modifications and equivalents which fall within the scope of the claims are embraced by the claims.

What is claimed is:

1. A diagnostic method for diagnosing behavior of an elongated body having a distal end and a proximal end in a biological lumen of a living body, the diagnostic method comprising:
   inserting the elongated body into the biological lumen of the living body from the distal end;
   detecting, with an X-ray system, energy having passed through the living body after irradiating the living body with the energy from the X-ray system;
   identifying, by a control unit, a position of the distal end of the elongated body in the living body by the detected energy having passed through the living body;
   calculating, by the control unit, an amount of deviation of the identified position of the distal end of the elongated body, the amount of deviation of the identified position of the distal end of the elongated body being an amount proportional to a length from an expected position of the distal end of the elongated body in a proper state in which a tortuosity of the elongated body has not occurred to the identified position of the distal end of the elongated body in which the tortuosity of the elongated body has occurred;
   issuing, with a notifying unit, a warning when the amount of deviation of the identified position of the distal end of the elongated body is equal to or greater than a preset threshold; and
   stopping, by the control unit, the calculation of the amount of the deviation of the identified position of the distal end of the elongated body after the issuance of the warning by the notifying unit; and
   moving the elongated body in a proximal direction within the biological lumen of the living body after the issuance of the warning by the notifying unit to eliminate the tortuosity of the elongated body.

2. The diagnostic method according to claim 1, further comprising:
   detecting a proximal length that is a length in a longitudinal direction regarding the elongated body located outside the living body; and
   identifying the expected position of the distal end of the elongated body based on a position of the distal end of the elongated body identified by the energy detected in the X-ray system and the proximal length.

3. The diagnostic method according to claim 1, further comprising:
   inserting the elongated body from a radial artery and reaching an artery of a lower limb in the inserting of the elongated body into the living body; and
   detecting the tortuosity of the elongated body in an ascending aorta of the living body.

4. The diagnostic method according to claim 1, wherein the expected position of the distal end of the elongated body is at least part of coordinate data of the biological lumen, the diagnostic method further comprising:
   detecting the elongated body outside of the biological lumen from the amount of deviation of the distal end of the elongated body.

5. The diagnostic method according to claim 1, further comprising:
   issuing the warning by a visual sense or an auditory sense when the amount of deviation is equal to or greater than the preset threshold.

6. The diagnostic method according to claim 1, wherein the elongated body is a guiding catheter, the diagnostic method further comprising:
   inserting an other elongated body into the guiding catheter.

7. The diagnostic method according to claim 1, further comprising:
   irradiating an inside of the living body with the energy from outside of the living body; and
   detecting, from outside of the living body, the energy having passed through the living body.

8. A control method of a diagnostic system configured to diagnosis behavior of an elongated body having a distal end and a proximal end in a living body, the control method comprising:
   inserting the elongated body into a biological lumen of the living body from the distal end;
   causing an X-ray system to carry out irradiation with energy;
   causing the X-ray system to detect the energy;
   receiving information on the detected energy from the X-ray system and identifying a position of the distal end of the elongated body from the information;
   calculating an amount of deviation of the position of the distal end of the elongated body, the amount of deviation of the position of the distal end of the elongated body being an amount proportional to a length from an expected position of the distal end of the elongated body in a proper state in which a tortuosity of the elongated body has not occurred to the identified position of the distal end of the elongated body in which the tortuosity of the elongated body has occurred;

causing a notifying unit to carry out a notification by a visual sense or an auditory sense according to the calculated amount of deviation of the identified position of the distal end of the elongated body;

stopping the calculation of the amount of the deviation of the identified position of the distal end of the elongated body after the issuance of the warning by the notifying unit; and moving the elongated body in a proximal direction within the biological lumen of the living body after the issuance of the warning by the notifying unit to eliminate the tortuosity of the elongated body.

9. The control method according to claim 8, further comprising:

detecting a proximal length that is a length in a longitudinal direction regarding the elongated body located outside the living body; and identifying the expected position of the distal end of the elongated body based on the position of the distal end of the elongated body identified by the energy detected by the X-ray system and the proximal length.

10. The control method according to claim 8, further comprising:

inserting the elongated body from a radial artery and reaching an artery of a lower limb in the inserting of the elongated body into the living body; and detecting the tortuosity of the elongated body in an ascending aorta in the detecting of the amount of deviation of the identified position of the distal end of the elongated body.

11. The control method according to claim 8, wherein the expected position is at least part of coordinate data of a biological lumen of the living body, the control method further comprising:

detecting the elongated body outside of the biological lumen from the amount of deviation of the identified position of the distal end of the elongated body.

12. The control method according to claim 8, further comprising:

issuing the notification with the notification unit by the visual sense or the auditory sense when the amount of deviation is equal to or greater than a preset threshold.

13. The control method according to claim 8, further comprising:

irradiating an inside of the body with the energy from outside of the living body with the X-ray system; and detecting from outside of the living body, the energy having passed through the living body with the X-ray system.

* * * * *